US 7,563,566 B2

(12) United States Patent
Woerner et al.

(10) Patent No.: US 7,563,566 B2
(45) Date of Patent: Jul. 21, 2009

(54) STABILIZATION OF $H_2O_2$ UNDER ALKALINE CONDITIONS FOR USE IN LUMINESCENCE, FLUORESCENCE AND COLORIMETRIC ASSAYS FOR ENHANCED DETECTION OF PEROXIDASE TYPE ASSAYS

(75) Inventors: Thomas M. Woerner, Westminster, MD (US); Joseph A. Rosebrock, Union Bridge, MD (US); Charles W. Hewitt, Blackwood, NJ (US); Heidi L. Woerner, Westminster, MD (US)

(73) Assignee: SurModics, Inc., Eden Prairie, MN (US)

( * ) Notice: Subject to any disclaimer, the term of this patent is extended or adjusted under 35 U.S.C. 154(b) by 183 days.

(21) Appl. No.: 11/648,911

(22) Filed: Jan. 3, 2007

(65) Prior Publication Data

US 2007/0264647 A1  Nov. 15, 2007

Related U.S. Application Data

(63) Continuation of application No. 10/141,177, filed on May 9, 2002, now Pat. No. 7,381,797.

(60) Provisional application No. 60/289,517, filed on May 9, 2001.

(51) Int. Cl.
*C12Q 1/00* (2006.01)
*C12Q 1/70* (2006.01)
*C12Q 1/68* (2006.01)
*C12Q 1/26* (2006.01)
*C12Q 1/30* (2006.01)
*C12Q 1/28* (2006.01)
*A61K 35/14* (2006.01)

(52) U.S. Cl. .................... 435/4; 435/5; 435/6; 435/25; 435/27; 435/28; 530/385

(58) Field of Classification Search ............... 435/4, 435/25, 27, 28, 5, 6; 530/385
See application file for complete search history.

(56) References Cited

U.S. PATENT DOCUMENTS

| 3,853,470 | A | 12/1974 | Morin et al. |
| 3,912,593 | A | 10/1975 | Barker et al. |
| 4,302,534 | A | 11/1981 | Halmann et al. |
| 4,318,980 | A | 3/1982 | Boguslaski et al. |
| 4,539,294 | A | 9/1985 | Metcalfe et al. |
| 4,868,106 | A | 9/1989 | Ito et al. |

(Continued)

OTHER PUBLICATIONS

Dansen et al., "Peroxisomes in human fibroblasts have a basicpH," Nature Cell Biology, vol. 2, Jan. 2000, pp. 51-53, Macmillan Magazines, London, England.

(Continued)

*Primary Examiner*—Jezia Riley
(74) *Attorney, Agent, or Firm*—Pauly, Devries Smith & Deffner, L.L.C.

(57) ABSTRACT

The invention relates to stannous halide stabilized and/or enhanced alkaline solutions to be used in combination with calorimetric, luminescent and fluorescent assays. The buffered solutions stabilize hydrogen peroxide at a pH greater than 7.0 and preferably greater than 9.0. By stabilizing and/or enhancing hydrogen peroxide in the buffer system, the compositions used in such assays may have a higher shelf-life and provide enhanced detection of the subject analyte.

16 Claims, 5 Drawing Sheets

U.S. PATENT DOCUMENTS

| | | |
|---|---|---|
| 4,954,435 A | 9/1990 | Krauth |
| 5,078,672 A | 1/1992 | Dougherty et al. |
| 5,171,668 A | 12/1992 | Sugiyama |
| 5,217,710 A | 6/1993 | Williams et al. |
| 5,362,633 A | 11/1994 | Pugia |
| 5,436,133 A | 7/1995 | Fujita et al. |
| 5,736,349 A | 4/1998 | Sasaki et al. |
| 5,736,497 A | 4/1998 | Steiner |
| 6,120,554 A | 9/2000 | Patton et al. |

OTHER PUBLICATIONS

Van Eyk et al., "The Isolation and Partial Charactization of Catalase and a Peroxidase Active Fraction from Human White Adipose Tissue," Int. J. Biochem, vol. 24, No. 7, pp. 1101-1109, 1992, Pergamon, Exeter, England.

Mueller et al., "Determination of Catalase Activity at Physiological Hydrogen Peroxide Concentrations," Analytical Biochemistry 245, pp. 55-60, 1997, Academic Press, Orlando, Florida.

Lazrus et al., "Automated Fluorometric Method for Hydrogen Peroxide in Atmospheric Precipitation," Analytical Chemistry, vol. 57, No. 4, Apr. 1985, pp. 922-926, American Chemical Society, Washington, DC.

Strategene Catalog (1988) p. 30.

International Search Report dated Dec. 12, 2002, issued in PCT/US02/14448.

US 7,563,566 B2

STABILIZATION OF H₂O₂ UNDER ALKALINE CONDITIONS FOR USE IN LUMINESCENCE, FLUORESCENCE AND COLORIMETRIC ASSAYS FOR ENHANCED DETECTION OF PEROXIDASE TYPE ASSAYS

CROSS-REFERENCE TO RELATED APPLICATIONS

This application is a continuation of Ser. No. 10/141,177, filed May 9, 2002, now U.S. Pat. No. 7,381,797,which claims priority under 35 U.S.C. § 119 to U.S. Provisional Application 60/289,517 entitled "Stabilization of $H_2O_2$ Under Alkaline Conditions For Use in Luminescence, Fluorescence And Colorimetric Assays For Enhanced Detection of Peroxidase Type Assays" filed May 9, 2001, the entire content of which is hereby incorporated by reference in its entirety.

FIELD OF THE INVENTION

The invention relates to methods, compositions and kits for use in luminescence, chemifluorescence and colorimetric assays which use or comprise a stannous halide at a pH about 7.0 or greater.

BACKGROUND OF THE INVENTION

This invention relates to an assay or detection method which employs an enzyme linked detection endpoint signaling system for the detection and measurement of compounds of interest in assay systems employing ligand binding techniques.

Such ligand binding techniques depend upon the facility inherent in biological molecules, such as receptors, antibodies and nucleic acids, to bind with a high degree of specificity to their respective analogous partner ligand. Owing to this specificity, such techniques have found widespread application in the detection and measurement of many entities ranging from simple chemicals to complex biological molecules, including peptides, proteins, carbohydrates and nucleic acids. Consequently, the technique of ligand binding has become one of the most important tools for biological research and diagnostic assays.

In such ligand binding systems, the specific binding reaction occurs when the ligand is presented to the ligand partner compound. Examples include the antibody-antigen reaction, and the hybridization of complementary nucleic acid sequences. A key feature inherent to all ligand binding assay systems is that, in order to monitor the progress of such binding and thus to obtain a qualitative and/or quantitative indication of the degree of such binding, it is necessary to label, either directly or indirectly, at least one of the ligand partners participating in the ligand binding reaction. This labeled ligand can then be employed to generate a measurable signal by which the reaction is monitored. The relative quantity of signal generated by the labeled ligand will be proportional to the quantity of labeled ligand present and thus can serve to indicate the concentration of the labeled ligand. Examples of such signal generators used include radioactive nuclides ($^{125}I$, $^3H$, $^{14}C$, $^{32}P$, etc.), chemiluminescent or fluorescent compounds (acridinium esters, lanthanide chelates) and enzymes (peroxidase, phosphatase).

Numerous non-radioactive methods have been developed to avoid the hazards, and inconvenience and disposal problems posed by radioactive materials. Examples of non-radioactive labels include: (1) enzymes that catalyze conversion of a chromogenic substrate to an insoluble, colored product (e.g. catalase, horseradish peroxidase, and the like) or catalyze a reaction that yields a fluorescent or luminescent product, and (2) direct fluorescent labels (e.g. fluorescein, isothiocyanate, rhodamine, Cascade blue), which absorb electromagnetic energy in a particular absorption wavelength spectrum and subsequently emit visible light at one or more longer (i.e., less energetic) wavelengths.

In the case of enzymes as primary signal generators, the action of the enzyme (e.g., peroxidase) on an appropriate substrate may itself lead to the generation of a secondary signal which is, for example, chemiluminescent or fluorescent in nature. In this situation, the role of the labeling enzyme is either direct, (i.e., to convert the substrate itself from an inactive to an active, and therefore, detectable compound) or indirect (i.e., to convert the substrate from an inactive to active substance, which is itself an initiator or co-factor in the conversion of an inactive to active compound). An example of the direct substrate is the direct action of alkaline phosphatase on stable dioxetanes, where removal of a phosphate group renders the dioxetanes unstable with a consequent release of quantifiable luminescence. An example of an indirect substrate is the indirect action of peroxidase on luminol, where luminescence is generated from enzyme-catalyzed production of an active oxygen species by breakdown of the peroxide (e.g., $H_2O_2$) substrate.

Of those systems which have found the most widespread application, the signal intensity can be low thus limiting the scope of application; in order to overcome this problem, such systems preferably use enhancers (e.g., para-iodo-phenol) or amplifiers (e.g., fluorescent polymers) to increase the complexity of these signal generating methods.

Methods based on enzyme-linked analytes offer the best sensitivity, as a single enzyme molecule typically has a persistent capacity to catalyze the transformation of a chromogenic or luminescent substrate into detectable product. With appropriate conditions and incubation time, a single enzyme molecule can produce a large amount of product and hence yield considerable signal amplification.

Chemiluminescent compounds which have been used in these assays include aminophthalhydrazides, acridans, acridinium esters and dioxetanes. U.S. Pat. No. 5,593,845 discloses, for example, chemiluminescent N-alkylacridancarboxylate derivatives which allow the production of light from the acridan by reaction with a peroxide and a peroxidase. U.S. Pat. No. 5,670,644, discloses improved acridan compounds which, upon reaction with a peroxidase enzyme and a peroxide compound, are converted into a more persistent, intermediate acridinium compound, wherein the center ring is aromatic, which subsequently undergoes a rapid chemiluminescent reaction when the pH is raised.

Additional compounds typically used with peroxidase include, but are not limited to 3,3',5,5'-tetramethylbenzidine (TMB), luminol, 2,2'-azinodi(3-ethyl benathiazoline sulfonic acid) (ABTS), 3'3-diaminobenzidine-(DAB), and 3-amino-9-ethylcarbazole (AEC).

Among the enzymes used in enzyme-linked detection methods such as immunoassays, detection of oligonucleotides and nucleic acid hybridization techniques, the most commonly used is horseradish peroxidase (HRP). Aminosubstituted cyclic phthalhydrazides (e.g., luminol and isoluminol) react with $H_2O_2$ and a peroxidase enzyme catalyst (e.g., horseradish peroxidase) under basic conditions to emit of light. This reaction has been used as the basis for analytical methods for the detection of $H_2O_2$ and for detecting-peroxidase. One problem with the system is that $H_2O_2$ is unstable in conditions of a pH greater than 7.0. However, the reaction preferably occur under alkaline conditions. Consequently, methods and compositions are needed which enhance $H_2O_2$ stability and/or activity at a pH greater than about 7.0, but which do not quench or otherwise inhibit the reaction.

Traditionally, compositions such as HF and other acids have been used to quench the reaction. The presence of fluoride in these reactions was considered to be responsible for terminating the reaction which produces a colorimetric, a luminescent, or a fluorescent label. Consequently, reagents comprising fluoride were not considered as suitable for use in these reactions.

In unrelated technology, colloidal stannic oxides, which are generated from Sn(II) and Sn(IV) chlorides, were reportedly used to stabilize phosphorus-free and boron-free cleaning compositions solutions which contained hydrogen peroxide (U.S. Pat. No. 5,736,497).

In the area of dental products, stannous chloride has been used to stabilize gels comprising hydrogen peroxide, sodium fluoride and a bicarbonate (U.S. Pat. No. 5,217,710).

U.S. Pat. No. 5,783,382 discloses methods for stably storing an indicator and an enzyme under sealed conditions using disoxidants, such as tin (II) salts. This is distinguishable from the instant invention which teaches stabilization of the substrate, hydrogen peroxide ($H_2O_2$).

SUMMARY OF THE INVENTION

Therefore, notwithstanding what has previously been reported in the literature, there exists a need for improved methods of, compositions and kits for luminescent, fluorescent and colorimetric assays, wherein a peroxide (e.g., $H_2O_2$) can be more accurately detected either by improving its activity and/or stability. By the addition of stannous halides to the kits and compositions used in fluorescent, luminescent and calorimetric peroxidase-catalyzed assays, the storage time and sensitivity of the system is improved. Additionally, the methods of using the kits, compositions and methods disclosed will greatly improve detection of compounds in peroxidase catalyzed assays. The kits and compositions and use thereof described herein will improve the stability and/or activity of an assay at standard temperature, may lead to a shelf-life of greater than six months when stored at 4° C., is inexpensive, allows for an easily measurable activity (e.g., colorimetric, fluorescent or luminescent), permits high substrate turnover and is unaffected by the n improved composition for use in a fluorescent and luminescent or a colorimetric assay. The composition comprises a heme containing protein, a peroxide, a peroxide stabilizing and/or enhancing amount of a stannous halide and an alkaline buffer. This composition comprises an amount of stannous halide sufficient to stabilize and/or enhance the peroxide under alkaline conditions. Additional embodiments include compositions where the stannous halide is a stannous fluoride or a stannous chloride ranging in amount from 0.005% to about 5%, and more preferably from about 1 ml per liter to about 50 ml per liter. In another embodiment, the heme containing protein is contemplated to be either a catalase, a peroxidase, a hemoglobin, a myoglobin, a ferritin, or a cytochrome oxidase, wherein the peroxidase is preferably horseradish peroxidase.

The alkaline buffers contemplated for use with this composition include but are not limited to a phosphate buffer, an aminomethylpropanediol buffer, a glycine-sodium hydroxide buffer, a barbitol buffer, a tricene buffer, a Bis-Tris buffer, a Tris buffer, an imidazole buffer, a sodium tetraborate decarbohydrate buffer, a sodium carbonate buffer or a CHAPS buffer.

Another object contemplated is to provide for an improved kit and an improved method for using the kit for conducting an assay for detecting, for example, the presence or concentration of a heme containing protein in a sample which comprises in one or more containers (a) a substrate which is rendered detectable by said heme containing protein, (b) a peroxide, (c) an alkaline buffer, and (d) a stannous halide.

It is also an object of the invention to provide an improved method of conducting an assay for the presence or concentration of an analyte in an aqueous sample comprising (1) admixing with said sample a heme containing protein which is coupled to a compound which binds specifically to said analyte; (2) removing unbound heme containing program protein in said sample after said mixing; (3) admixing a composition comprising a peroxide, a stannous halide, a substrate and an alkaline buffer; and (4) measuring the amount of detectable substrate obtained, wherein detectable substrate obtained is indicative of the presence or concentration of said analyte.

Another object of the invention is to provide an improved method wherein one skilled in the art can detect for the presence or concentration of a heme containing protein in a sample comprising adding to said sample a composition comprising (1) hydrogen peroxide, (2) a substrate, (3) a stannous halide, and (4) an alkaline buffer; and measuring the amount of detectable substrate obtained by said reaction wherein said detectable substrate is indicative of the presence or concentration of said heme containing protein.

It is yet another object of the present invention to provide for a method for detecting the presence or concentration of a peroxide in a sample comprising adding to said sample a composition comprising (1) a heme containing protein, (2) a substrate, (3) a stannous halide, and (4) an alkaline buffer; and measuring the amount of detectable substrate obtained by said reaction wherein said detectable substrate is indicative of the presence or concentration of said peroxide.

It is yet another object of the invention to provide a method for performing in situ hybridization with a first nucleic acid which is attached to an indicator and wherein said first nucleic acid can hybridize to a second nucleic acid in a cell or a tissue sample obtained from a subject comprising the steps of obtaining a cell or tissue sample from said subject; digesting said cell or said tissue sample with a protease; performing in situ hybridization on said cell or said tissue sample obtained from the prior step with said first nucleic acid which specifically hybridizes to said second nucleic acid; incubating said cell or said tissue sample from the prior step in a composition comprising (a) a peroxide, (b) a heme containing protein, (c) a stannous halide, and (d) an alkaline buffer; and detecting said indicator bound to said first nucleic acid which is reacted by said heme containing protein.

With the foregoing and other objects, advantages and features of the invention that will become hereafter apparent, the nature of the invention may be more clearly understood by reference to the following detailed description of the preferred embodiments of the invention and to the appended claims.

BRIEF DESCRIPTION OF THE DRAWINGS

FIG. 3. Western blots using TMB (FIG. 3A) or DAB (FIG. 3B).

DETAILED DESCRIPTION OF THE INVENTION

Figure 1:
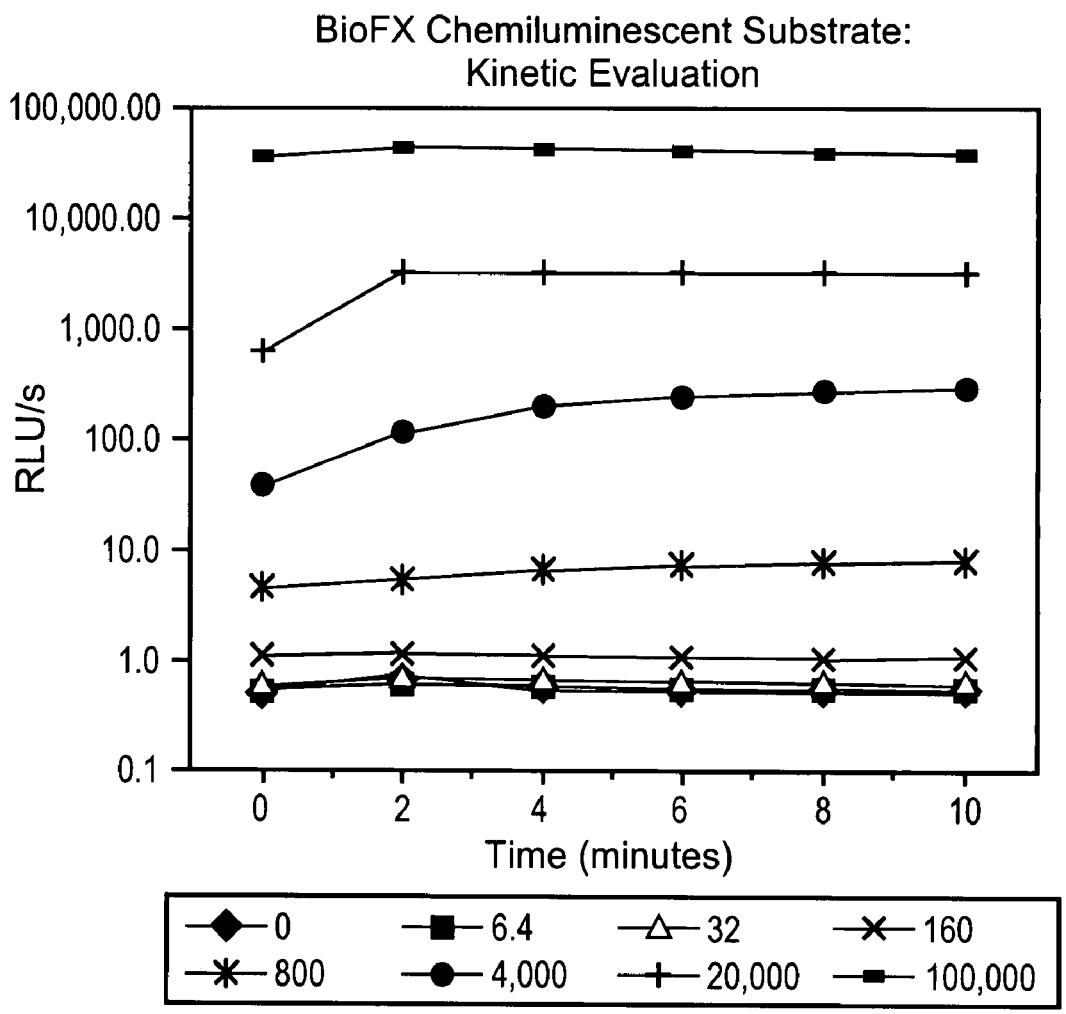
FIG. 1. Chemiluminescent substrate kinetic evaluation. The relative light units (RLUs) per second are plotted versus time (minutes).

In one embodiment, the invention is directed to a one-step method of performing colorimetric assays. In another embodiment, the invention is directed towards a two-step assay method for use with luminescent agents such as luminol. In one embodiment, these assays, regardless of the indicator used (e.g., luminescent, fluorescent or colorimetric) are performed using buffers comprising a stannous halide, preferably stannous fluoride ($SnF_2$ is also known as tin fluoride or tin difluoride), as a means of stabilizing and/or enhancing hydrogen peroxide or other peroxide compounds used in compositions and kits for assays employing heme containing proteins, with a preferred heme containing protein being peroxidase. In the examples set forth herein, wherein peroxidase is used, it is contemplated that other heme containing proteins can be substituted for peroxidase, as would be known in the art. In the examples wherein $SnF_2$ is utilized, it is also contemplated that other stannous halides, such as for example stannous chloride ($SnCl_2$), can be substituted therefore, as would be known in the art.

The components of this system are the enzyme, which can be chemically coupled either directly or indirectly to a ligand, hydrogen peroxide ($H_2O_2$), a stannous halide, and a compound (i.e., indicator) which reacts with peroxide to produce the signal (i.e., luminescent, fluorescent or colorimetric). A composition comprising an alkaline buffer, $H_2O_2$ or other peroxide, a stannous halide and an indicator (e.g., colorimetric or chemiluminescent) are admixed under alkaline conditions (a pH greater than 7.0). Preferably, the pH range of the admixture is greater than 7.0 to about 11.0, with a preferred pH range of about 8.0 to about 10.0.

The preferred peroxidase enzyme to be used is horseradish peroxidase (HRP). However, other peroxidases are commercially available and can be used. The invention also contemplates the use of any heme containing protein, such as but not limited to myoglobin, hemoglobin, peroxidase, catalase, ferritin, and cytochrome oxidases.

The labeling enzyme or other heme containing protein (i.e., peroxidase) can be linked directly to the ligand by chemical coupling using established linking techniques. Alternatively, the enzyme may be indirectly linked to the ligand by an intermediate ligand binding system.

One example of such an indirect system involves the utilization of the established avidin-biotin system, in which these two substances themselves participate in a binding reaction with extremely high affinity. In this example, one component, for example biotin, is chemically linked to ligand (e.g., antibody or a nucleic acid sequence, many examples of such biotinylated ligands are available commercially), and the peroxidase enzyme is linked to avidin. Following the ligand binding reaction, the ligand complex, containing the biotinylated ligand, is exposed to the enzyme-linked avidin, allowing the capture of enzyme by the ligand complex. The detectable reaction can then occur by the subsequent exposure of this indirectly enzyme labeled ligand complex to a solution containing the desired substrate/indicator.

The methods, compositions and kits of the invention can be used to analyze biological samples. For example, biological samples taken from a subject (e.g., human or other living organism) can be analyzed using the methods, compositions and kits of the invention by in situ hybridization, immunohistochemistry, immunoassay, western blot, northern blot, Southern blot, DNA hybridization assay, DNA sequence analysis, colony hybridization, gene expression analysis, high throughput drug screening, detection of infectious agents or pathogens and the like. Biological samples can be any sample containing DNA, RNA or protein, such as blood, plasma, serum, urine, semen, saliva, cell lysates, tissue extracts and the like. Other types of biological samples which can be assayed include food samples and environmental samples such as soil or water.

The amount of biological sample needed for detection can vary. The compositions and kits described herein can be used to analyze samples consisting of amounts less than about a nanogram ($10^{-9}$) to about a picogram ($10^{-12}$). Preferably, the assay compositions and methods can detect about a femtogram ($10^{-15}$).

Unless stated otherwise, chemiluminescent compounds, chemifluorescent compounds, bioluminescent compounds and chromagens can all be used with the kits, compositions and processes described herein. It would be evident to one of ordinary skill that, for example, a chemiluminescent compound can be substituted for a chromagen, depending on the degree of quantification or qualification required for the analyte being assayed.

A. Definitions and Acronyms

By "colorimetric" is meant a signal which is light absorbing and can be detected between about 400 to about 700 nm.

By "fluorescent" is meant a light signal (photon) generated by exciting a fluorophore at a given wavelength and detecting the light at an emission wavelength. By "chemifluorescent" is meant a fluorescent signal initiated by a chemical reaction. By "luminescent" is meant to include both chemiluminescent and bioluminescent reactions.

By "chemiluminescent" is meant a light signal generated by a chemical reaction. A preferred chemiluminescent agent is luminol (5-amino-2,3-dihydrophthalazine-1,4-dione). When luminol and peroxidase are reacted, for example, in the presence of hydrogen peroxide, amino phthalic acid in the excited state is produced. This acid produces a light energy at 425 nm when returning to the ground stage.

By "bioluminescent" is meant a compound capable of emitting light when excited to an electronic excited state. The light can be emitted either as fluorescence, when decaying from a singlet excited state, or as phosphorescence, when decaying from a triplet excited state is. One example of a bioluminescent compound is luciferin (e.g., firefly luciferin).

By "analyte" is meant a substance the presence or amount of which is to be measured in a sample by an assay. Analytes include organic and biological molecules to which a specific binding partner having a specific binding affinity exists. Exemplary analytes include drugs, hormones, pesticides, pesticide metabolites, DNA, RNA, oligonucleotides, antibodies, antibody fragments, antibody-DNA chimeras, antigens, haptens, proteins, carbohydrates, lectins, receptors, avidin, streptavidin and biotin. Exemplary binding partners include antigen-antibody, hapten-antibody or antibody-antibody pairs, complementary oligonucleotides or polynucleotides, avidin-biotin, streptavidin-biotin, hormone-receptor, lectin-carbohydrate, IgG-protein A, nucleic acid-nucleic acid binding protein and nucleic acid-anti-nucleic acid antibody.

By "stannous halide" is meant a tin compound comprising halogen atoms such as fluorine, chlorine, bromine or iodine atoms. The formula for a stannous halide would be $SnX_2$, wherein X represents any halogen. Preferred stannous halides are $SnCl_2$ and $SnF_2$, with the most preferred being $SnF_2$.

By "peroxide" is meant a compound containing an O—O bond, preferably hydrogen peroxide ($H_2O_2$). However, other peroxides contemplated include, but are not limited to urea peroxide, persulfate, perborate salts, percarbonate, a metal peroxide (e.g., $Na_2O_2$), or a generated peroxide. By "generated peroxide" is mean a peroxide that is generated by a chemical or biological reaction.

By "stannous halide stabilizing amount" is meant a concentration of stannous halide sufficient to prevent or inhibit the degradation of a peroxide (e.g., $H_2O_2$) in an alkaline solution. The solution optionally also contains an indicator and/or heme containing protein.

By "stannous halide enhancing amount" is meant a concentration of stannous halide sufficient to enhance the detection of the sample being analyzed which is in an alkaline solution as compared to a system which lacks the stannous halide. Preferably the degree of enhancement is statistically significant.

By "heme containing protein" is meant any protein with an ion which can react with a peroxide.

By "peroxidase" is meant any enzyme which catalyzes the reduction of hydrogen peroxide by a substrate which loses two hydrogen atoms. Preferred forms of peroxidase include horseradish peroxidase (HRP is derived from the roots of *Amoracia rusticana*), and other plant and fungal peroxidases. Other forms of peroxidase include those from the microorganism of imperfect fungi *Arthromyces ramosus* (see U.S. Pat. No. 5,084,381), secretory plant peroxidases, secretory fungal peroxidases. See for example, Welinder, "Superfamily of plant, fungal and bacterial peroxidases," *Curr Opin. Struct. Biol.* 2: 388-393 (1992). Typically, the peroxidase catalyzes the oxidation by hydrogen peroxide ($H_2O_2$) of a substrate. The substrates include but are not limited to ascorbate, ferrocyanide, cytochrome C and the leuco form of many dyes. The reaction is as follows:

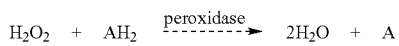

wherein "A" is the oxidized and detectable analyte.

By "substrate" and "indicator" are meant the substrate for peroxidase. These substrates include chromagens, chemifluorescent compounds, chemiluminescent compounds and bioluminescent compounds, including but not limited to those listed in Table 1 below.

TABLE 1

| Chemiluminescent Compounds | Chromagen Compounds | Chemifluorescent Compounds | Bioluminescent Compounds |
|---|---|---|---|
| diacyl hydrazides | 4CN | HPA | luciferin |
| isoluminol | 5AS | HPPA | firefly luciferin |
| luminol | ABTS | Amplex ™ Red | *Cypridina* luciferin |
| polyphenols | AEC | | |
| purpurogallin | DAB | | |
| pyrogallol | Hanker-Yates | | |
| umbelliferone | o-dianisidine | | |
| | OPD | | |
| | PPD | | |

TABLE 1-continued

| Chemiluminescent Compounds | Chromagen Compounds | Chemifluorescent Compounds | Bioluminescent Compounds |
|---|---|---|---|
| | TMB | | |
| | Vector SG | | |
| | Vector Nova | | |
| | Vector VIP | | |

Abbreviations:
ABTS 2,2'-azinodi[3-ethylbenzthiazoline] sulfonate
AEC 3-amino-9-ethylcarbazole
Amplex ™ Red 10-acetyl-3,7-dihydroxyphenoxazine
DAB 3,3',4,4'-diaminobenzidene
ELFIA enzyme linked fluorescent immunoassay
ELISA enzyme linked immunosorbent assay
HPA hydroxyphenylacetic acid
HPPA 3-p-hydroxyphenylproprionic acid
HRP horseradish peroxidase
OPD o-phenylenediamine
PPD p-phenylenediamine
TMB 3,3',5,5'-tetramethylbenzidine
4CN 4-chloro-1-naphthol
5AS 5-aminosalicyclic acid By "enhancer" is meant a compound or composition which improves detection of peroxidase-based assays. These enhancers can be used for luminescent, chemifluorescent, chemiluminescent and colorimetric reactions to increase or enhance the intensity of the color produced or the light emitted. For example, enhancers have been employed in conjunction with the use of luminol and other detectable agents to increase the intensity of light emitted or chromagen detected (See, for example the polymeric quarternary salt enhancers for luminol cited in U.S. Pat. No. 5,994,073).

By "accelerator" is meant a catalyst which decreases the energy of activation for a reaction.

By "binding pair" is meant two substances which exhibit a mutual binding affinity. Bind pairs include but are not limited to ligand-receptor, antigen-antibody, hapten-antibody or antibody-antibody pairs, complementary oligonucleotides or polynucleotides, avidin-biotin, streptavidin-biotin, hormone-receptor, lectin-carbohydrate, IgG-protein A, nucleic acid-nucleic acid binding protein and nucleic acid-anti-nucleic acid antibody.

By "alkaline buffer" is meant a solution with a pH greater than 7.0. Such alkaline buffers include but are not limited to those set forth in the examples, phosphate, aminomethylpropanediol, glycine-sodium hydroxide, barbitol, Bis-Tris, sodium carbonate, Tris, tricine imidizide and CHAPS buffers.

B. Assays Utilizing Peroxidase

It is contemplated that the techniques, and kits and compositions therefor will have widespread utility within the field of ligand binding assays. There are several distinct categories of ligand binding assay systems in which this invention may thus have application, and examples of these are listed below.

(1) Immunoassays where the unique specificity of antibodies for their respective partner antigens is exploited to enable quantification of the antigen or antibody. The rate and degree of reaction of ligand binding is proportional to the amount of antigen and/or antibody present and is monitored by labeling of one of the partner ligands. Immunoassays are well known to those skilled in the art. See for example Tijssen, *Practice and Theory of Enzyme Immunoassays: Laboratory Techniques in Biochemistry and Molecular Biology* vol 15, (Elsevier Amsterdam, 1990) and Harlow et al., *Antibodies: A Laboratory Manual* (Cold Spring Harbor 1988). Immunoassays also include immunohistochemistry, wherein labeled antibodies or fragments thereof are used to bind to tissue or cells from a subject to detect the presence of a protein. Immunohistological methods are known in the art. See for example, Wick et al., *Monoclonal Antibodies in Diagnostic Immunohistochemistry*, (Marcel Dekker, 1988); and Colvin et al. (eds.), *Diagnostic Immunopathology* ($2^{nd}$ ed., Raven Press 1995). In peroxidase reactions, the peroxidase is typically conjugated to the antibody in a ratio of about 4:1.

Immunoassays using the compositions and kits described herein can be used with, but are not limited to, enzyme linked immunosorbent assay (ELISA) reactions, ELISPOT, cellular ELISAs (CELISA), western blots, detection in a gel, antibody capture assays, antigen capture assays, sandwich assays, etc. Immunoassay procedures in which a peroxidase catalyzes the oxidation of a substrate by peroxide are well known in the art. The immunoassay methods described herein contemplate using a peroxide (e.g., $H_2O_2$) containing liquid which also has a stabilizing and/or activity enhancing amount of a stannous halide. Stabilizing amounts of stannous halides is that which increasing the shelf-life of a composition comprising a peroxide at alkaline pH as compared to the same composition which lacks a stannous halide. Stabilizing amounts of stannous halides may include about 0.001% to about 5% stannous halide. More preferably, the amount of stannous halide is 0.005% to about 3%. More preferably still, the stannous halide is present in the alkaline composition in amount ranging from about 1 mg/liter to about 50 mg per liter, and most preferred, the amount ranges from about 5 mg/liter to about 25 mg/liter. For example, stannous fluoride can be used in an amount of 1 mg/L to about 50 mg/L, and more preferably in an amount ranging from about 5 mg/liter to about 25 mg/liter. Similar amounts can be used with stannous chloride and other stannous halides. These concentrations are also suitable for enhancing the detection of the sample.

In general, the immunoassays using the methods and compositions of the invention may be used to detect or quantify an antigen, an antibody or a hapten. In this disclosure, the substance to be determined is referred to as the analyte. The analyte preferably has an anti-analyte, which binds substantially specifically to the analyte. Thus, if the analyte is an antigen, a suitable anti-analyte would be an antibody that specifically recognizes and binds to said antigen. If the analyte is a hapten or a peptide, a suitable anti-analyte can be an anti-hapten antibody or anti-peptide antibody, respectively. If the analyte is an antibody, a suitable anti-analyte can be an antigen recognized by that antibody or another antibody that specifically recognizes and binds to the first antibody.

Antibodies useful in the invention as anti-analytes may be either monoclonal or polyclonal. Preparing such antibodies is well known in the art. See for example, Harlow et al., *Antibodies: A Laboratory Manual* (Cold Spring Harbor, 1988).

The immunoassays may be carried using any conventional sandwich or competitive procedure known in the art. The assay may be either heterogeneous or homogeneous, and may be carried out in the liquid phase or on a solid support. For example, in a typical sandwich assay, a first antibody may be affixed to a solid support such as a dipstick, membrane, microtiter plate well or the inside wall of a tube.

Preferably, the antibody coated support may be further coated with an inert protein (e.g., casein or albumin) to block substantially all remaining binding sites on the support and thereby suppress non-specific binding of the label directly or indirectly to the support.

A solution suspected of containing an antigen, hapten or other composition detectable by immunoassay is added, and conditions conducive to binding the antigen to the antibody are provided. An indicator, which can optionally be attached to a second antibody having a peroxidase covalently conjugated thereto, is added. After binding of the second antibody to the antigen, the solid support having affixed thereto an antibody-antigen-peroxidase-labeled antibody bound fraction is contacted with a solution containing peroxide, the stannous halide and the indicator. The indicator is oxidized by the peroxide in a reaction catalyzed by the peroxidase component of the bound fraction on the solid support to form a color (if using a colorimetric assay). The color is indicative of the presence of the antigen. The intensity of the color (or light if using a luminescent assay) is directly proportional to the concentration of the antigen in the liquid.

In a typical competitive assay of the invention, a limited quantity of the antibody on the solid support may be contacted with the liquid suspected of containing the antigen which includes a known quantity of the antigen having peroxidase conjugated thereto. The antigen and enzyme-labeled antigen bind to the antibody on the support in direct proportion to their concentrations in the solution. Thus, after binding, the support contains an antibody-antigen bound fraction and an antibody-peroxidase labeled antigen bound fraction. After separation of the support from the assay fluid phase, the bound fractions on the support may be contacted with peroxide and the indicator to cause formation of a color. Alternatively, if chemiluminescent, bioluminescent or chemifluorescent agents are used instead, the agent is to be detected based on the release of photons or luminescence. However, in the competitive assay of the invention, the color formed is inversely proportional to the concentration of analyte in the liquid.

It is evident from the above discussion that the methods and compositions comprising a stannous halide may also be used to assay the amount of peroxidase present in a liquid. In this embodiment of the invention, a liquid suspected of containing a peroxidase may be contacted with peroxide and the indicator (i.e., chemiluminescent compound, chromagen, etc.) in the presence of a stannous halide, preferably $SnF_2$. The range of $SnF_2$ used is, for example, about 1 mg/L to about 50 mg/L, with a preferred concentration being about 5 mg/L to about 25 mg/L. These ranges could be similarly used for other stannous halides. The concentration of stannous halide used may vary depending on the final pH of the solution (e.g., a higher pH may require additional amounts of stannous halide).

Formation of color in the liquid is indicative of the presence of a peroxidase, and the intensity of the color (or other detectable indicator) provides a measurement of the concentration of the peroxidase.

In still another embodiment of the methods and compositions of the invention, stannous halides can be used in assays to determine the presence and/or amount of peroxide in a liquid or sample. Concentrations would be the same discussed elsewhere in the application. For example, a sandwich immunoassay for an analyte may be performed on a solid support using as the label an enzyme (i.e., peroxidase) which releases hydrogen peroxide into the assay fluid phase at a rate proportional to the peroxidase concentration. Measurement of the hydrogen peroxide released may be carried out by adding HRP or other peroxidase and the substrate (e.g., chromagen, chemiluminescent compound, etc.) of the invention whereby the peroxide may be determined by the color formed and may be related to the analyte.

Substrate. A suitable substrate for use is chosen which meets the requirements of the assay being performed. Substrates can be colorimetric, fluorescent or luminescent (i.e., chemiluminescent or bioluminescent). For colorimetric products, the substrates can be insoluble or soluble. For example, typically insoluble reaction products are desired for membrane-based assays, such as dot blots, western blots, northern blots, Southern blots and variations thereof as are known in the art. In the case of dot blots, an insoluble colored dot is produced at the site of reaction. This can be a visual assay that is detectable using densitometry and can be permanent, depending on the substrate chosen. Insoluble reaction products however are not practical for solution immunoassay as performed in 96-well plates (e.g., ELISAs). Use of soluble reaction products are better suited for solution immunoassays such as ELISAs.

Choice of substrates depends on the sensitivity desired, timing requirements and the detection device to be used. If high sensitivity is needed (i.e., able to detect low amounts of analyte), the most desirable substrates typically produce intensely colored reaction products at very fast reaction rates.

For assays that require a large dynamic range (i.e., typical analyte amounts span a wide range of concentrations), a substrate that produces reaction products over a long period of time (e.g., about 15-30 minutes) and results in a broad range of color intensities depending on the amount of analyte present is the most desirable. For assays that are intended to be stopped (i.e., a chemical inhibitor is added to the reaction after a defined amount of time that stops further color development and allows detection to be performed with a reasonable time period), a substrate having a "slow" reaction rate (i.e. 15-30 minutes to complete) is most desirable. This slow reaction rate allows the technician or the equipment to start the reaction and stop the reaction at a reasonable pace. However, if kinetic analysis of the enzyme-substrate reaction is to be employed, a substrate having a "fast" reaction rate ($\leq 5$ min.) is most desirable. In this case, the substrate is added and the rate of conversion of substrate colored reaction product is immediately measured.

The most common substrates that produce insoluble products are TMB (3,3',5,5'-tetramethylbenzidine), DAB (3,3',4, 4'-diaminobenzidine) and 4CN (4-chloro-1-naphthol). The most common substrates that produce soluble reaction products are TMB (a dual function substrate), ABTS (2,2'-azino-di [3-ethylbenzthiazoline]sulfonate), OPD (o-phenylenediamine) and PPD.

Many factors affect the measurement of enzymatic activity. The most important factors include temperature, pH, ionic strength, buffer composition, substrate depletion, build-up of product inhibitors, increasing back-reaction as product concentration increases, denaturation of the enzyme and even exposure to light. For ELISAs, the most important factors are reaction time, temperature and exposure to light.

After the addition of a termination solution and/or prior to reading the optical density (OD), preferably the well contents should be thoroughly admixed to assure both complete cessation of the reaction (endpoint assay only) and even dispersion of the colored reaction product.

TMB is a highly sensitive substrate. Due to its rapid reaction rate, it is ideally suited for on-line kinetic analysis. It produces a blue color measurable at 650 nm. TMB can also be used in endpoint assays, by stopping the reaction with, for example, 1 M phosphoric acid. A yellow reaction product is formed upon acidification that is measurable at 450 nm.

ABTS is considered an all-purpose substrate. Although it is less sensitive than either TMB or OPD, it has the widest working range of any substrate currently available for peroxidase. The reaction product for ABTS is a blue-green compound which is measurable at about 405-410 nm. Its reaction rate is suitable for endpoint assays and easily stopped with 1% sodium dodecyl sulfate (SDS), which does not change the color or the absorbence of the reaction product.

OPD is slightly less sensitive than TMB and has a reaction product which is yellow and is detectable at about 490 nm. All of the above colormetric agents can be used in combination with stannous halides. Preferable ranges are in the amount of about 1 mg/L to about 50 mg/L.

Fluorescent immunoassays (ELFIA) are simply a variation of colorimetric ELISAs. An enzyme converts a substrate to a reaction product that fluoresces when excited by light of a particular wavelength. The relative fluorescence units (emitted photons of light) that are detected are typically proportional to the amount of analyte being measured. In comparison to the colorimetric ELISA, fluorescent immunoassays are only slightly more sensitive. However, they widen the dynamic range of the assay by allowing very high readings to be accurately measured, as opposed to the about 2.0 to about 4.0 OD limit imposed with use of colorimetric assays.

The two most common fluorogenic substrates used for ELFIA's utilizing peroxidase as the enzymatic label are HPA (hydroxyphenylacetic acid), HPPA (3-p-hydroxyphenyl-proprionic acid), and Amplex™ Red. Both require the addition of $H_2O_2$ to produce a fluorescent product. HPPA is the most widely used fluorogenic peroxidase substrate. Its fluorescent product has an excitation wavelength of 320 nm and an emission wavelength of 404 nm. As contemplated herein, stannous halides can be utilized in the range of 0.005% to about 3.0% and more preferably in a range of about 1 mg/L to about 50 mg/L in such fluorescent reactions to stabilize and/or enhance peroxides, such as $H_2O_2$.

Fluorometric assays are subject to several problems that either non-specifically reduce or enhance the signal output. Detection of fluorescence is susceptible to changes in pH, temperature, ion concentration, detergent concentration, drying and the solid matrix. These problems can lead to light scattering (i.e., caused by the emitted fluorescent light being bounced around as it comes in contact with molecules and/or particles in solution or with the surface of the microwell), background (e.g., sample components, diluent components, plate material, and miscellaneous contamination), quenching (i.e., a non-specific reduction in signal), and bleaching or fading (i.e., a reduction in signal caused by an excessively long excitation step).

Luminescent immunoassays, like fluorescent immunoassays, are variations of the standard ELISA. An enzyme converts a substrate to a reaction product that emits photons of light instead of developing a visible color. Luminescence is described as the emission of light from a substance as it returns from an electronically excited state to ground state. The various forms of luminescence (e.g., bioluminescence, chemiluminescence, photoluminenscence) differ the way the excited state is reached. For example, photoluminescence is simply fluorescence. The excitation is initiated by light at a particular wavelength. Bioluminescence is characterized by the use of a bioluminescent compound, such as luciferin or firefly luciferase. Chemiluminescence is light produced by a chemical reaction. It is believed that luminescence is the most sensitive detection method currently in use due to the ability of signal multiplication and amplification. Luminescent reactions are measured in relative light units (RLUs) that are typically proportionate to the amount of analyte present in a sample.

The most widely used enzyme for luminescent immunoassays is peroxidase. Peroxidase can be used with either bio- or chemiluminescent systems and is easily enhanced to permit prolonged detection of intense light.

A luminescent substrate is desirably chosen for its (1) low background luminescence in the ground state, (2) ability to produce intense light in its active state, (3) ability to produce stable light emission over a prolonged (minutes) period of time, and (4) commercial availability (quality and consistency). The substrate preferable is stable at room temperature during the duration of the assay.

Peroxidase has the most extensive list of suitable substrates for use in luminescent assay system. These include: (1) luminol (e.g., ECL™ system by Amersham), (2) polyphenols, and (3) luciferin. Peroxidase's reaction with luciferin is considered bioluminescence. In this reaction, peroxidase replaces the in vivo enzyme, luciferase. The other substrates are chemiluminescent compounds. Polyphenols are actually a class of substrates that include but are not limited to: pyrogallol, purpurogallin, gallic acid, and umbelliferone. All polyphenols are known for their excellent signal to noise ratio and extremely rapid light decay. Polyphenol and acridine ester substrates can only be used in conjunction with luminescent detectors equipped to handle "flash" reactions. The most popular substrate used for immunoassays is luminol. Luminol is commercially available in a stabilized form for use in western blotting, northern blotting, Southern blotting and various hybridization protocols. It is the most suited for clinical diagnostic tests due to its properties when used in an enhanced luminescence system. Commercially, luminol is typically provided with an enhancer (i.e., firefly luciferin, dehydroluciferin, phenols, naphthols, aromatic amines, p-hydroxycinnamic acid, or benzothiazoles) that protects the enzyme and allows the reaction to proceed for many minutes without substantial decay in light output. Phenol enhancers include mono-substitute phenols (e.g., p-iodophenol, p-bromophenol, p-chlorophenol) and di-substituted phenols (e.g., 2-chloro-4-bromophenol, 2,4-dichlorophenol, 3,4-dichlorophenol,) and p-phenylphenol. Napthol enhancers include 1,6-dibromo-2-naphthol and 1-bromonaphth-2-ol. Benzothiazole enhancers include, for example, 6-hydroxybenzothiazole and 2-cyano-6-hydroxybenzothiazole. Aromatic amine enhancers include for example N,N,N',N'-tetramethylbenzidine. Typically, light emission stabilizes in less than 2 minutes, and sustained emission lasts for approximately 20 minutes or more.

Enhanced luminescence is characterized by the following desirable features: intense light emission, prolonged light emission, low background, no preincubation step, and substrate can be added several minutes prior to detection. As long as commercial preparations of luminol are being used, control of the reaction pH typically is not a concern. However, incorporation of the stannous halides into the solution will help optimize the stability and/or enhance the activity of the kit, especially as the pH typically is stabilized at 8.5 (the pH at which maximum signal with the lowest background occurs) to allow optimal peroxidase activity (pH 5.5) and optimal light emission (pH 12.0) to occur. If needed, increasing concentrations of a stannous halide as conditions become more alkaline.

Therefore, if the pH varies above or below the desired amount (i.e., pH=8.5), either the enzymatic activity or the luminescent detection will be negatively affected. Peroxides however are typically unstable in alkaline conditions. Thus, compositions comprising stannous halides, such as $SnF_2$, which improve the stability and/or enhance the activity of $H_2O_2$ will also enhance assays using luminol.

As mentioned, luminol-based chemiluminescence is well suited for 96 well immunoassays, plus this system can also be utilized with DNA probe assays.

As discussed above, there are two distinct methods of detecting luminescence—flash and glow. Flash luminescence is transient in nature and reaches maximum light intensity within seconds (sec) or milliseconds (msec). Due to the speed at which the reaction occurs, it is necessary to start the reaction while the reactants are in front of the photomultiplier or light detection device.

Starting the reaction consists of adding substrate and complementary reagents or buffers including $SnX_2$ and subsequent mixing of all the assay components. Of paramount importance is the requirement that there be a constant time interval between the addition of the starting reagents and the time that the measurement takes place. For a 96 well plate assay, this requirement is met by coordinating this step within the reading chamber. Reagent addition and light measurement takes place in a step-wise manner one well at a time.

An alternate detection method is "glow luminescence", which is a steady-state kinetic approach to signal generation. Glow luminescence is actually a large number of transient signals that occur in sequence and result in a constant signal. Unlike colorimetric or fluorescent reactions, the light produced is not accumulated as color or fluorescence can be, so the light emitted is intense and the enzyme reaction prolonged in order to obtain sufficient signal. The positive aspects of glow luminescence are that (1) the reaction can be started outside of the detection instrument, thus eliminating the need for internal injection and mixing within the reader; (2) the procedure is simple; (3) the results are sensitive; (4) excellent enhanced substrate systems are commercially available; and (5) the procedure is highly suited for 96 well plate assay formats. This type of luminescent reaction can be measured using a luminometer, captured on photographic film, or recorded via image analysis.

Enzyme-substrate reaction time is relevant with regard to obtaining reproducible results. Even though glow reactions are expected to be stable for at least 20 minutes, results typically are more consistent from well-to-well and from plate-to-plate when the incubation time is shorter. Preferably, a two-minute stabilization period after substrate addition followed by immediately reading the plates is employed. Both signal strength and precision can be improved by optimizing the enzyme-substrate reaction incubation time. As is known in the art, luminescent reactions do not require a stopping step.

To quantitate ELISA assays or other assays using one of the above methods, one needs either a spectrophotometer (calorimetric), fluorometer (fluorescence) or luminometer (luminescence) to generate a standard curve.

(2) Nucleic acid analysis in which the unique specificity of nucleotide sequences for their respective complementary nucleotide sequences is exploited to enable identification and analysis of such sequences. This specificity has been utilized in examples such as DNA sequencing, DNA "fingerprinting", the identification of markers of genetically linked diseases, and the diagnostic identification of pathogenic organisms. These techniques have a requirement for the qualitative and sometimes quantitative identification of nucleotide sequence binding. Currently, a large proportion of the qualitative analysis of nucleotide binding is carried out using gels (e.g., polyacrylamide and agarose gels). One aspect of the invention is for using the kits, compositions and methods of the invention to improve detection of nucleic acid detection in gels or on membranes. Preferably, detection is by calorimetric means, however, bioluminescent, chemiluminescent, and chemifluorescent methods can also be employed.

Molecular biology techniques, in particular the analysis of nucleic acids by ligand binding, are well known to those skilled in the art. See for examples, Brown, *Essential Molecular Biology: A Practical Approach*, (Oxford University Press, Oxford, 1991); Ausubel et al., *Current Protocols in Molecular Biology*, (Greene Publishing Co., NY, 1995); Sambrook et al., *Molecular Cloning: A Laboratory Manual*, (2nd Ed. Cold Spring Harbor Laboratory Press, 1989); and *Short Protocols in Molecular Biology: A Compendium of Methods from Current Protocols in Molecular Biology* (Frederick M. Ausubel et al., April 1999).

Nucleic acid assays include northern blots (RNA detection), Southern blots (DNA detection), hybridization reactions, and high-throughput screening assays to detecting nucleic acids which bind to each other. The substrates of the invention can be bound directly to a nucleic acid or through an intermediate compound as would be known in the art. Typically, the substrates are attached either directly or indirectly to a probe, which hybridizes to a nucleic acid which is the analyte. Alternatively, the analyte itself can be labeled either directly or indirectly and further analyzed.

The conditions for detecting whether the analyte has been labeled would be the same as those discussed generally for nucleic acid reactions using peroxidase assays for luminescent, calorimetric or fluorescent reactions. The compositions and methods of the instant invention utilizing stannous halides, and especially $SnF_2$, under alkaline conditions can be used with any of these reactions. A preferred range of stannous halides include about 1 to about 50 mg/L, with a preferred pH range of about 8.0 to about 10.0.

Table 2 summarizes some of the commercially available indicators for use in peroxidase reactions and some of the associated application in which they can be used. From Table 2, it would be apparent to one of ordinary skill which assays (ELISA versus blot, etc.) work with the listed peroxidase substrates.

TABLE 2

| Peroxidase Substrate | Soluble/ Insoluble | Application[a] | Color |
|---|---|---|---|
| 4CN | insoluble | immunohistochemistry, blotting | blue |
| 5AS | soluble | ELISA | yellow |
| ABTS | soluble | ELISA | green |
| AEC | insoluble | immunohistochemistry, blotting | red |
| Amplex ™ Red | soluble | ELFIA | light fluorescence |
| DAB | insoluble | immunohistochemistry, blotting | brown or black |
| HPA | soluble | ELFIA | light fluorescence |
| HPPA | soluble | ELFIA | light fluorescence |
| luminol | soluble | blotting, ELISAs | light fluorescence |
| o-dianisidine | soluble | ELISA | yellow brown |
| OPD | soluble | ELISA | yellow |
| PPD | soluble | ELISA | yellow |
| TMB | insoluble/ soluble | immunohistochemistry, blotting, ELISAs | blue |
| Vector SG | insoluble | immunohistochemistry, blotting | blue-grey |
| Vector NovaRED | insoluble | immunohistochemistry, blotting | red |
| Vector VIP | insoluble | immunohistochemistry, blotting | purple |

[a]By blotting is meant to include, dot blots, western blots, northern blots, Southern blots, and variations thereof. By immunohistochemistry is meant to include detection using antibodies agents in cells and tissue as well as in situ hybridization.

In Situ Hybridization. In situ hybridization is a method of using nucleic acid probes for single copy sequences to detect chromosomal structural abnormalities or gene expression in tissue obtained from a subject. Typically, the tissue is prepared one of four ways: (1) fixed in formalin, as one would normally fix tissues for histology and embedded in wax and sectioned; (2) snap frozen and embedded in a special support medium for cryosectioning. The sections are subsequently lightly and rapidly fixed in paraformaldehyde just prior to processing for hybridization; (3) cells in suspension can be cytospun onto glass slides and fixed with methanol; and (4) prepared into metaphase chromosomal spreads which are normally fixed with a mixture of methanol and acetic acid.

The probes used to hybridize to the tissue or cells fall essentially into one of four types: (1) oligonucleotide probes produced synthetically, (2) single stranded DNA probes usually on the order of about 200 to 500 bp, (3) double stranded DNA probes, and (4) RNA probes/riboprobes. Methods of preparing these probes would be known in the art. See for example, *Short Protocols in Molecular Biology: A Compendium of Methods from Current Protocols in Molecular Biology* (Frederick M. Ausubel et al., April 1999).

The tissue sections regardless of how they are prepared are treated with an effective amount of a proteinase, preferably proteinase K. Proteinases remove the peroxidases present in the cells and tissue which would create background in any peroxidase assays. The time required for proteinase digestion of the tissue section will vary depending on the type of tissue and manner in which it was prepared. Also, certain tissue sections are more resistant to the effects of proteinase digestion than others. For example, it has been observed that normal tissues fixed in formalin are more refractory to protein digestion than tumor material derived from the same tissue type fixed in formalin. An "effective amount of proteinase" is that amount which will digest the tissue sufficiently such that a probe for single copy sequences can be detected. One skilled in the art could readily determine the length of time required for proteinase digestion and the effective amount of proteinase required by observing the level of signal obtained with in situ hybridization.

Hybridization of the detectable probes to the cells is conducted with a probe concentration of about 0.1-500 ng/µl, preferably 5-250 ng/µl. The probe concentration is greater for a larger nucleic acid (e.g., single- or double-stranded DNA).

The hybridization mixture will preferably contain a denaturing agent such as formamide, and non-specific human DNA, preferably derived from the placenta, which is used to block repeat sequences. The non-specific DNA is added at a concentration of 100 ng/µl to 2 µg/µl, more preferably 0.2-1 µg/µl, and most preferably about 0.25 to about 0.5 µg/µl, to compete out any repetitive portions of the probe.

The DNA in the tissues and the DNA probes are denatured either independently prior to hybridization or simultaneously. In general the denaturation is carried out by placing the tissues or DNA probes into a hybridization solution preferably containing a denaturing agent such as formamide and heating from 70° C. to 95° C. Preferably the concentration of formamide is from about 30% to about 70%, more preferably about 40% to about 60%. The temperature at which the tissues are held in order to achieve denaturation will vary according to the concentration of the denaturation agent. Surprisingly, it has been found that probes for single copy sequences do not need to be denatured prior to placement on the denatured tissue. Therefore, in a preferred embodiment the single copy probe is not denatured prior to hybridization.

In general, hybridization is carried out at 25° C. to 45° C., more preferably at 32° C. to about 40° C., and most preferably at about 37° C. to about 38° C. The hybridization step is conducted using the recommended hybridization buffer for the indicator being used and a $SnX_2$. The range of $SnX_2$ used for in situ hybridization is about 0.001% to about 5%, with a preferred range of about 1 mg/L to about 50 mg/L at a pH of about 8.0 to about 10.0.

Hybridization can be performed over about 0.25 to about 96 hours, more preferably 1-72 hours, and most preferably from about 4 to about 24 hours. Hybridization time will be varied based on probe concentration and hybridization solution content which may contain accelerators such as hnRNP binding protein, trialkyl ammonium salts, lactams, and the like. Slides are then washed with solutions containing a denaturing agent, such as formamide, and decreasing concentrations of sodium chloride or in any solution that removes unbound and mismatched probe.

The temperature and concentration of salt will vary depending on the stringency of hybridization which is desired. For example, high stringency washes may be carried out at 42-68° C., while intermediate stringency may be in the range of 37-55° C., and low stringency may be in the range of 30-37° C. Salt concentration for a high stringency wash may be 0.5-1×SSC (0.15 M NaCl, 0.015 M Na citrate).

For parafin fixed tissue, the detection incubation steps, are preferably carried out in a moist chamber at 23-42° C., more preferably at 25-38° C. and most preferably at 37-38° C. Labeled reagents are preferably diluted in a solution containing a blocking reagent, such as bovine serum albumin (BSA), nonfat dry milk, or the like. Dilutions may range from 1:10-1:10,000, more preferably 1:50-1:5,000, and most preferably at 1:100-1:1,000. The slides or other solid support may be washed between each incubation step to remove excess reagent.

Slides may then be mounted and analyzed by microscopy in the case of a colorimetric indicator. In the case of a fluorescent indicators, slides are preferably mounted in a solution which contains an antifade reagent, and analyzed using a fluorescence microscope.

(3) Protein analysis on gels (e.g., polyacrylamide gels) where proteins are sorted on the basis of physicochemical characteristics such as size or charge, and their qualitative identification is then achieved by probing with specific anti-protein antibodies or fragments thereof (western blotting). Presence of a particular protein is determined by the binding of an antibody to the protein or peptide it recognizes or under non-reducing conditions, potentially to a nucleic acid. The antibody or other agent used to detect the protein is labeled with a detectable substrate acted upon by peroxidase. Identification of ligand binding is commonly achieved by using chromagens with consequent limitations in sensitivity of detection. Such techniques are well known to those skilled in the art. See for examples, Walker, *New Protein Techniques: Methods in Molecular Biology*, vol 3 (Humana Press, Clifton N.J., 1988); and Harlow et al., (1988).

C. Enhancers, Surfactants and Additives

Enhancers. To enhance the chemiluminescent signal, and improve signal/noise (S/N) ratio to permit discrimination between background signals and positive target-responsive signals at very low levels, a water soluble enhancement agent is added to the sample prior to or concomitant with the introduction of the indicator. Examples of water-soluble enhancement agents include polymeric quaternary amines, neutral detergents and cationic detergents. Particularly effective are the polymeric onium salts, e.g., quaternary salts based on phosphonium, sulfonium and, preferably, ammonium moieties. These polymeric onium salts are disclosed in U.S. Pat. No. 5,547,836, as enhancement agents for 1,2-dioxetanes. Poly(vinylbenzyltributylammonium chloride) (TBQ) is particularly effective in increasing the chemiluminescent signal produced by the excited oxyanions.

Enhancers include, but are not limited to, D-luciferin, p-iodophenol, 1,2-dioxetanes, 4-phenylphenol p-phenylphenol, 2-hydroxy-9-fluorenone. For additional enhancers, see for example U.S. Pat. No. 5,206,149. Enhancers used to enhance the action of the peroxidase enzyme include 4-iodophenol and 4-phenylphenol, among others. Thus the kits, compositions and methods described herein optionally include the use of at least an enhancer depending on the indicator used.

The enhancers can optionally be used in combination with enhancement additives. For example, the polymeric quaternary salt enhancement agents taught in U.S. Pat. No. 5,994,073 can be used with such enhancement additives as conventional surfactants (e.g., cationic, anionic zwitterionic or neutral detergents), negatively charged salts, conventional solvents at low concentrations (e.g., alcohols or turpentine), and non-quaternary water-soluble polymers (e.g., poly(2-ethyl-Z-oxazoline)). The enhancers and enhancer additives can be used alone or in combination.

Surfactants and Additives. The use of surfactants as additives in the luminescence assays is advantageous and lead to further improvement of analytical sensitivity. Nonionic surfactants useful in the practice of the present invention, include by way of example, polyoxyethylenated alkylphenols, polyoxyethylenated alcohols, and polyoxyethylenated ethers. Cationic surfactants, including quaternary ammonium salt compounds, are also useful in increasing the level of chemiluminescence emitted.

Thus, embodiments of the methods, compositions and kits disclosed herein also contemplate, optionally, the use of surfactants and additives. The surfactants and/or additives employed would be based on the indicator used.

Fluorescent energy acceptors. Additionally, fluorescent energy acceptors optionally can be employed in the methods and kits contemplated, as suitable. Fluorescent energy acceptors can be used to shift the maximum emission to longer wavelengths (e.g., red-shifting) and/or to increase the quantity of luminescence emitted. Fluorescers can be covalently linked to a compound, or alternatively, can be added to reaction solution as a separate species, or linked to a polymer or electrostatically associated with a micelle or a polymer.

Although the present invention has been described in detail with reference to examples below, it is understood that various modifications can be made without departing from the spirit of the invention, and would be readily known to the skilled artisan. The following examples are given for purposes of illustration only, and are not meant to limit the scope of the invention.

EXAMPLES

Example 1

Imidazole Buffer

The imidazole buffer is preferably used with colorimetric assays at a pH of preferably about 7.0 to about 8.5. However, imidazole buffers can be used with other indicator systems which utilize peroxide.

0.68 g Imidazole (pH=7.6)

10 µl $SnF_2$ (100 mg $SnF_2$, 2 mL 6 N HCl and 2 mL $H_2O$)

The components were admixed and brought to a pH of 7.3 with 6 N HCl. 0.5 ml of 2% $H_2O_2$ was added. 40 µl $SnF_2$ was added and then water was added quantity sufficient (Q.S.) to bring to a final volume of 100 ml.

$SnF_2$ is added at two distinct points to the buffered $H_2O_2$ composition rather than in one dosage because the second addition causes a significant difference in the intensity of the colors, than observed when the $SnF_2$ is added to the buffer at once.

Example 2

Imidazole Buffer for DAB

A stannous fluoride alkaline buffer comprising imidazole which can be used with DAB was prepared as follows:

Admixed 800 mL $H_2O$, 6.8 g imidazole and 100 μl $SnF_2$ (100 mg $SnF_2$ in 2 ml 6 N HCl and 2 ml $H_2O$). Brought the pH to 7.3 with 6 N HCl. Then added 5 mL of 2% $H_2O_2$ and 400 μl $SnF_2$. Brought the final volume to 1 liter. This buffer was used with DAB but can be used with any chromagen as would be known in the art. The buffer can also be used with chemiluminescent indicators.

Example 3

Imidazole Buffer for Luminol

Admixed 800 ml $H_2O$, 6.8 g imidazole and 100 μl $SnF_2$ (100 mg $SnF_2$ in 2 ml 6 N HCl and 2 ml $H_2O$). Brought the pH to the desired pH. For example, the composition can be brought to a pH of 7.5, 8.5 or 9.5. When the final pH is obtained, then added 5 ml of 2% $H_2O_2$ and 400 μl $SnF_2$ and Q.S. to a final volume of 1 liter.

This buffered, hydrogen peroxide composition can be brought to the pH needed for the indicator being used. For example, for luminol a higher pH is preferred (e.g., pH of 9.5 or higher).

Example 4

Bis-Tris Buffer

A Bis-Tris buffer can be prepared for use with any indicator, but is preferably used with chemiluminescent agents, due to the higher pH. Bis-Tris buffers preferably have a pH ranging from about 8.0 to about 10.0.

Admixed 750 ml $H_2O$ and 28.2 g Bis-Tris Propane (Sigma; FW=282.3). The solution had a pH of 11.11. Then added 5 mL of 2% $H_2O_2$ and 500 μl $SnF_2$ (100 mg $SnF_2$ in 2 ml 6 N HCl and 2 ml $H_2O$). The addition of the $SnF_2$ lowered the pH to 10.67. Adjusted the pH of the solution to 9.5 with 6 N HCl. Q.S. to a final volume of 1 L and a final pH of 9.5.

Unlike with the imidazole buffer, the $SnF_2$ can be added to the Bis-Tris buffer at the same time. There is no significant difference observed in the intensity of the indicator used when the $SnF_2$ is added at two different stages or at the same time.

Example 5

Sodium Tetraborate Decarbohydrate Buffer

This buffer can be used with any indicator system, but is preferably used with chemiluminescent reagents which require a higher pH, and preferably a pH of about 8.0 to about 11.0.

Admixed 750 ml $H_2O$ with 38.1 g sodium tetraborate decarbohydrate (Aldrich). The solution was warmed slightly to dissolve the sodium tetraborate decarbohydrate and was determined to have a pH of 9.28. Then 5 ml of 2% $H_2O_2$ was added along with 500 μl $SnF_2$ (100 mg $SnF_2$ in 2 ml 6 N Hcl and 2 ml $H_2O$) and mixed into the solution, which lowered the pH to 9.27. The final pH was adjusted to 9.0 using 6 N HCl. Q.S. the final volume to 1 L.

Like the Bis-Tris buffer, the $SnF_2$ can be added all at once, without any difference in the intensity of the indicator used.

Example 6

Sodium Carbonate Buffer

This buffer can be used with any indicator system, but is preferably used with chemiluminescent reagents which require a higher pH. Sodium carbonate buffers preferably have a pH of about 8.0 to about 11.0.

750 ml $H_2O$ and 10.6 g sodium carbonate (Sigma) were admixed producing a solution with a pH of 11.12. 500 μl of $SnF_2$ (100 mg $SnF_2$ in 2 ml 6 N HCl and 2 ml $H_2O$) and 5 mls of 2% $H_2O_2$ were added, which lowered the pH to 11.0. The final volume was brought to 1 liter and the final pH was adjusted to 9.5 using 6 N HCl.

As with the sodium tetraborate decarbohydrate stannous fluoride buffer, the $SnF_2$ can be added all at once in this system, without altering the intensity of the indicator used.

Example 7

Tris Buffer

This buffer can be used with any indicator system, but is preferably used with chemiluminescent reagents, which require a higher pH. Tris buffer preferably have a pH of about 8.0 to about 11.0.

750 ml $H_2O$ and 12.1 g Tris Base (Sigma) were admixed resulting in a solution with a pH of 10.6. 500 μl $SnF_2$ (100 mg $SnF_2$ in 2 ml 6 N HCl and 2 ml $H_2O$) and 5 ml of 2% $H_2O_2$ were added to the solution, which reduced the pH to 9.75. The final pH of the stannous fluoride solution was adjusted to 9.5 with 6 N HCl and the final volume of the solution was brought to 1 liter.

As with the sodium tetraborate decarbohydrate stannous fluoride buffer, the $SnF_2$ can be added all at once in this system, without altering the intensity of the indicator used.

Example 8

CHAPS Buffer

A CHAPS buffer can be used with any indicator system, but is preferably used with chemiluminescent reagents which require a higher pH. CHAPS buffers preferably have a pH of about 8.0 to about 11.0.

In this case, 750 ml $H_2O$ is mixed with 61.4 g (3-[(3-cholamidopropyl)-dimethylammonio]-1-propane sulfonate (CHAPS). The final volume would then be brought to 1 liter. 500 μl $SnF_2$ (100 mg $SnF_2$ in 2 ml 6 N HCl and 2 ml $H_2O$) and 5 ml of 2% $H_2O_2$ are added to the buffer. The pH then is adjusted to a final pH of about 9.5 using 6 N HCl. The buffered $H_2O_2$ solution can be adjusted to a different pH depending on the needs of the indicator as would be known to the skilled artisan.

As with the sodium tetraborate decarbohydrate stannous fluoride buffer, the $SnF_2$ can be added all at once in this system, without altering the intensity of the indicator used.

Example 9

HRP Sensitivity Evaluation Using a Sodium Carbonate Buffer

A buffer comprising 0.02 M $Na_2CO_3$, $SnF_2$ (100 mg $SnF_2$ in 2 ml 6 N HCl and 2 ml $H_2O$) in an amount as described for examples 1-7, water, 1.0 mM luminol, and 0.25 mM p-coumaric acid (pCA) and $H_2O_2$ was used. 10 μl of the HRP sample was added per well. Then 100 μl of $Na_2CO_3$ buffer/luminol mixture comprising the above constituents was injected into each well. Immediately thereafter, the luminometer read the amount of luminescence produced for a period of 10 seconds.

In Table 3 below, the amount of luminescence detected given the amount of horseradish peroxidase (HRP) used is presented.

TABLE 3

| HRP (pg/ml) | Luminescence after 10 sec. | Luminescence after 5 min. | Luminescence after 10 min. |
|---|---|---|---|
| Dil. | 10.845 | 5.91 | 5.218 |
| $10^0$ | 10.245 | 6.235 | 4.891 |
| $10^1$ | 10.312 | 6.332 | 5.239 |
| $10^2$ | 11.829 | 7.589 | 6.243 |
| $10^3$ | 24.355 | 38.761 | 42.513 |
| $10^4$ | 474.095 | 1729.49 | 1,659.04 |
| $10^5$ | 21,221.3 | 24,421.9 | 21,592.4 |
| $10^6$ | 483,384 | 304,276 | 247,289 |

Figure 2:
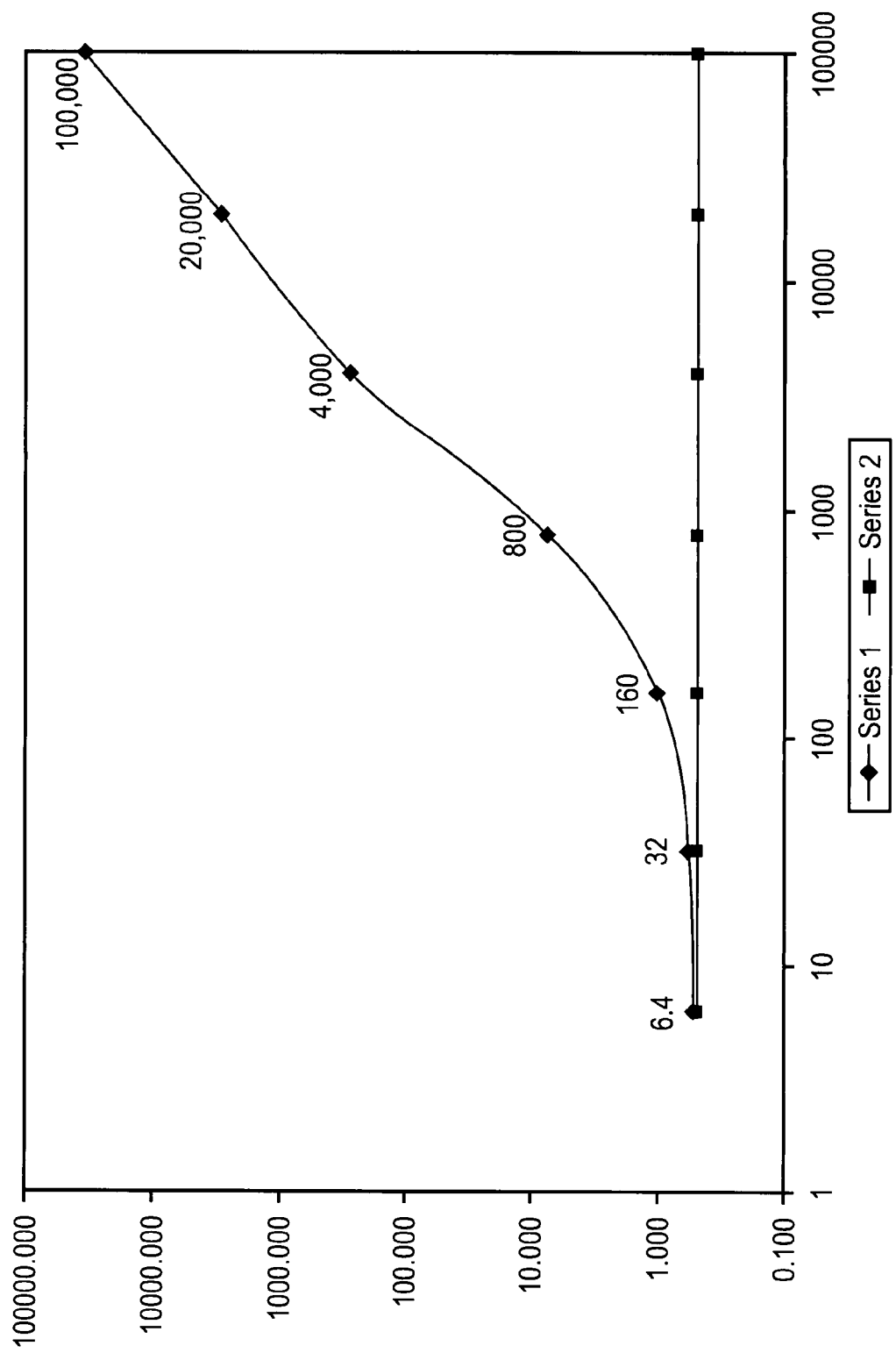
FIG. 2. The RLU's at 10 minutes is plotted versus the concentration of horseradish peroxidase (pg/ml).

The kinetic evaluation of luminol as relative luminescence units (RLUs) v. time (min) is presented in FIG. 1. The RLUs values obtained at 10 minutes are plotted over concentration of HRP as displayed in FIG. 2. FIG. 2 demonstrates that as little as 32 pg of HRP can be detected using the stannous fluoride stabilized buffer system described in this example.

Example 10

HRP Sensitivity Evaluation Using a Bis-Tris Buffer

A Bis-Tris buffer system was prepared as follows: 1 ml 100 mM Bis-Tris (final concentration of 20 mM), 2 ml d$H_2O$, 0.5 ml 10× luminol, 0.5 ml pCA, 10 μl 2% $H_2O_2$ and 100 μl 10% Triton X-100 were admixed. 10 μl was added to each well. Then 100 μl of the Bis-Tris-luminol composition was injected into each well. Detection of the luminescence produced by the reaction was recorded by a luminometer at 10 sec, 5 min and 10 min after injection. Table 4 presents the detected luminescence (RLUs) using this system.

TABLE 4

| HRP (pg/ml) | Luminescence after 10 sec. | Luminescence after 5 min. | Luminescence after 10 min. |
|---|---|---|---|
| Dil. | 0.543 | 1.026 | 0.963 |
| $10^0$ | 0.458 | 1.183 | 0.81 |
| $10^1$ | 0.531 | 1.55 | 1.116 |
| $10^2$ | 0.803 | 2.102 | 1.628 |
| $10^3$ | 4.106 | 7.768 | 6.86 |
| $10^4$ | 106.127 | 744.509 | 743.71 |
| $10^5$ | 14,752.6 | 21,513.6 | 19,489.1 |
| $10^6$ | 512,303 | 355,789 | 242,937 |

Using the same buffer, the data below in Table 5 presents the decay values every 2 minutes after injection of the luminol-containing solution.

TABLE 5

| pg/ml | t = 0 min | t = 2 min | t = 4 min | t = 6 min | t = 8 min | t = 10 min |
|---|---|---|---|---|---|---|
| 0 | 0.535 | 0.755 | 0.541 | 0.505 | 0.495 | 0.490 |
| 6.4 | 0.529 | 0.614 | 0.564 | 0.533 | 0.520 | 0.522 |
| 32 | 0.629 | 0.731 | 0.661 | 0.660 | 0.606 | 0.573 |
| 160 | 1.089 | 1.168 | 1.091 | 1.065 | 1.003 | 1.010 |
| 800 | 4.601 | 5.266 | 6.502 | 6.956 | 7.224 | 7.378 |
| 4,000 | 39.032 | 112.491 | 193.058 | 238.016 | 261.202 | 271.450 |
| 20,000 | 619.551 | 3,206.954 | 3,243.458 | 3,145.342 | 3,033.677 | 2,908.414 |
| 100,000 | 35,605.55 | 42,173.08 | 40,231.33 | 38,295.47 | 36,392.68 | 34,666.29 |

Example 11

Intensity Measurements for Wester Blot Immunostaining Using Anti-Heat Shock Protein-70 (HSP-70) Antibody and Stannous Fluoride Enhanced DAB Western blotting was performed to compare results when stannous fluoride was used as compared to blots wherein no stannous fluoride was present. In this experiment, heat shock proteins were serial diluted from 0.10 μg-0.04 μg. Proteins were separated by SDS gel electrophoresis. Electrophoresis was run for 2 hours. Proteins were transferred onto membrane by transblotting performed for 6 hours at 4° C. Bio-Rad Laboratories Immunoblot Membrane PVMF membranes (7×8.5 cm, Cat. No. 1620174; Hercules, Calif.) were blocked with 1.0% bovine serum albumin (BSA) in 1×PBS (pH=7.4) with 0.5% Tween-20 (vol/vol) for one hour at room temperature (RT), then washed three times in 1×TBS (pH 7.4) and dried. Immunoblots were performed using primary antibody (i.e., 200 μg/ml, mouse anti-human HSP-70, Cat. No. SC-24; Santa Cruz) at a 1:2,000 dilution and incubated at RT for 2 hours. Blots were then washed three times in 1×TBS (pH 0.7.4). Secondary antibody (i.e., 1.5 mg/ml biotin-goat anti-mouse IgG, Cat. No. 81-6540; Zymed Laboratories, South San Francisco, Calif.) was then used at a 1:2,000 dilution. Blots were incubated at RT in the presence of the secondary antibody for 30 minutes in 1% BSA in 1×PBS with 0.5% Tween-20 (vol/vol), followed by 3 washes in 1×TBS (pH 7.4). The Strepavidin-HRP labeling system (Cat. No. 43-8323; Zymed Laboratories) was used according to manufacturer's instructions at a 1:1,000 dilution (in a diluent comprising 1% BSA in 1×PBS with 0.5% TWEEN-20, vol/vol), incubated for 15 minutes at RT and then the blots were washed three times in 1×TBS.

Figure 3A:
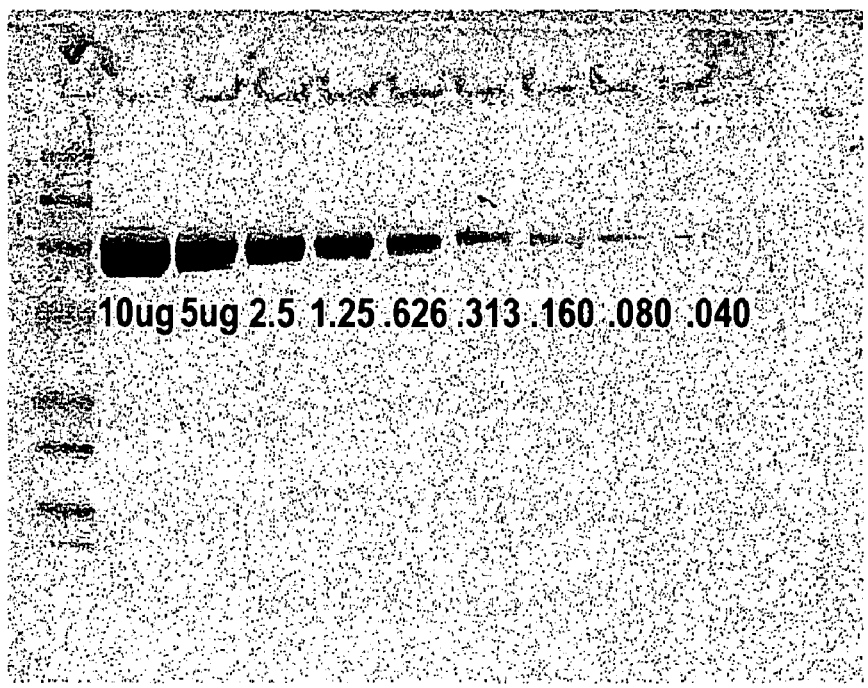
FIG. 3A has the molecular weight marker in Lane 1 and dilutions of 0.04, 0.08, 0.160, 0.3125, 0.625, 1.25, 2.5, 5 and 10 μg in Lanes 2-10, respectively.

For color detection, substrates tested included TMB One Component Membrane Substrate (BioFX Inc., Owings Mills, Md.) according to manufacturer's recommended instructions (without stannous fluoride). 180 µg/ml DAB (BioFX) was used in combination with the stannous fluoride enhanced/ stabilized formulation as described in Examples 1 and 2 above at a pH of 7.5. TMB or DAB chromagens were utilized until bands developed. The reaction developed within 5 minutes. The quality and quantity of staining was assessed by titration. Two representative immunoblots are depicted in FIGS. 3A and B. A lower number represents a greater dilution of the antigen and increased sensitivity of staining by the chromagen substrate.

Figure 3B:
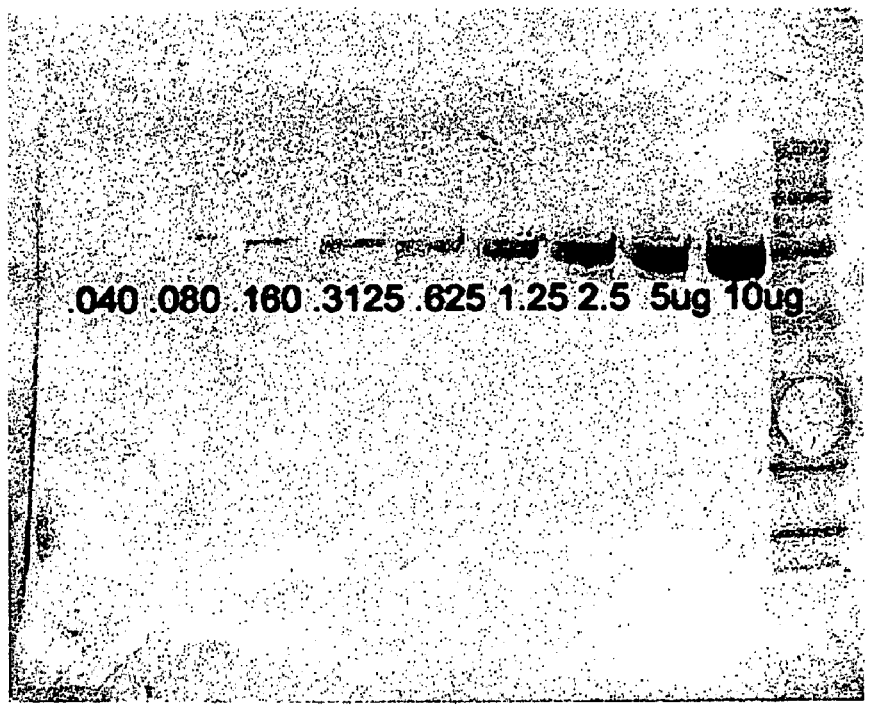
FIG. 3B has the dilutions of 0.04, 0.08, 0.160, 0.3125, 0.625, 1.25, 2.5, 5 and 10 µg in Lanes 1-9 respectively and molecular weight marker in Lane 2.

The differences in quality and intensity of immunostaining using a well-known and highly sensitive chromagen substrate (i.e., TMB without stannous fluoride) versus the stannous fluoride enhanced formulation with DAB are shown in FIG. 3. The difference between the $SnF_2$ enhanced DAB and TMB was negligible. The titrations demonstrated that both chromagens detected the antigen at concentrations of 0.04 to 0.08 µg. This result was surprising and unexpected as TMB is generally regarded as one of the most sensitive chromagen substrates available. Thus, the $SnF_2$-DAB enhanced formulation produced staining of intensity and sensitivity comparable to TMB, and greater than that typically obtained by DAB in the absence of $SnF_2$.

Example 12

Intensity Measurements for Tissue Immunostaining with Anti-Cytokeratin Antibodies and Stannous Fluoride Enhanced DAB Human skin was fixed in formalin and embedded in parafin using standard methods known in the art. Specimens were sectioned at 4-8 µm and placed on slides. Parafin was then removed from the tissue by placing the slides in an oven for one hour at 60° C. The slides were then sequentially treated with (1) xylene immersion for 5 minutes, (2) a second xylene immersion for 5 min., (3) immersion in absolute alcohol for 30 sec., (4) a second immersion in absolute alcohol for 30 sec., (5) immersion in 95% alcohol for 30 sec., (6) a second immersion in 95% alcohol for 30 sec., and (7) rinsing the slides in running tap water.

Immunostaining was performed to detect cytokeratin using an antibody cocktail (mouse anti-human cytokeratin (cocktail), Cat. No. D802, Lot # 071M) produced by BioGenex (San Ramon, Calif.) and the DAKO Autostainer (DAKO, Carpinteria, Calif.) according to manufacturer instructions. Tissue slides were retrieved in Dako antigen retrieval formulation for 10 min. at 95° C.-100° C. The slides are then cooled in 1×TBS wash buffer. The slides were then incubated in an endogenous inhibitor solution for 15 minutes (i.e., 3% $H_2O_2$ in methanol). The slides were blocked using normal goat serum for 15 minutes (1 ml goat serum and 2 ml of Diluent wherein the diluent is 1% BSA in 1×PBS with 0.5% TWEEN-20 vol/vol). Slides were washed once with 1×TBS. The slides were then incubated for 60 min. at RT with the primary antibody, mouse anti-human cytokeratin cocktail (BioGenex) at a 1:500 dilution. After incubation, the slides were rinsed twice with 1×TBS buffer. The slides were then incubated with a secondary antibody (i.e., biotin labeled goat anti-mouse IgG, Cat. No. 81-6540; Zymed Laboratories) for 30 minutes at RT at a final concentration of 3 kg/ml. The slides were washed again and then detected using the Strepavidin-HRP (same as in Example 11), at a 1:1,000 dilution for 15 minutes at RT. The slides were rinsed once with 1×TBS buffer.

The substrate, DAB (675 µg/ml), at various test formulations was then added in the presence or absence of the stannous fluoride buffer described in Example 2 above. Two conventional DAB formulations (DAB1 and DAB2) (DAB Stable Liquid Substrate, Cat. No. DABM-10 of Moss Laboratories, Pasadena, Md. and Stable DAB, Cat. No. 54-11-00, Lot # WL004 of Kirkegaard Perry Laboratories, Gaithersburg, Md., respectively) were used as the controls. DAB was incubated for 5 minutes and then slides were rinsed with TBS.

The slides were counterstained to see the cellular and cytoarchitectural features. Counterstaining was performed as follows. Slides were immersed for 1 min. in hematoxylin (Sigma, St. Louis, Mo.; Cat. No. GHS3-128) as suggested by the manufacturer. The slides were then rinsed well using running tap water. The slides were quickly dipped in a solution containing 1% HCl in 70% EtOH. Slides were again well rinsed in running tap water followed by 10 rapid immersions (dips) in 0.3% ammonia in water. The slides were again well rinsed followed by a rapid immersion in 95% ethanol. The slides were then immersed three times, 30 sec. each, in absolute alcohol.

The quality and quantity of staining was assessed by digital image analysis. Four representative areas were chosen from each preparation. There areas were digitized and the intensity of the stain was analyzed in integrated optical density units (IOD) using ImagePro Plus (Media Cybernetics, Silver Spring, Md.). A higher number represents a more intensely DAB-stained image. The results were statistically analyzed using Kruskal-Wallis one-way ANOVA on ranks and the Student-Newman-Keuls multiple comparison technique using SIGMA-STAT® (Jandel Scientific, San Rafael, Calif.).

Figure 4A:
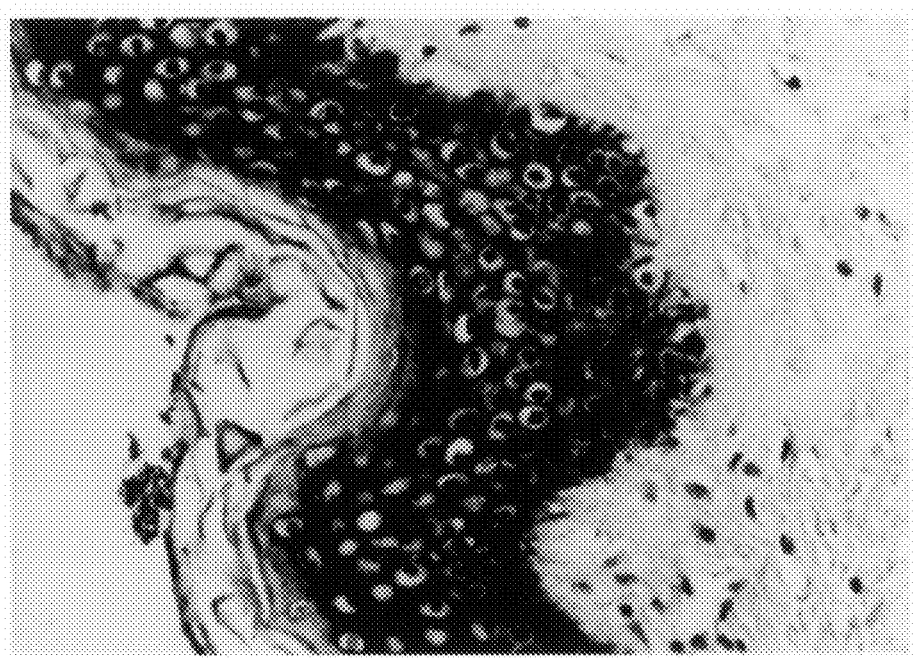
FIG. 4. Immunostaining of skin using DAB in a $SnF_2$ formulation (FIG. 4A) or DAB in a conventional formulation DAB2 (Kirkegaard Perry Laboratories, Gaithersburg, Md.) (FIG. 4B).
Figure 4B:
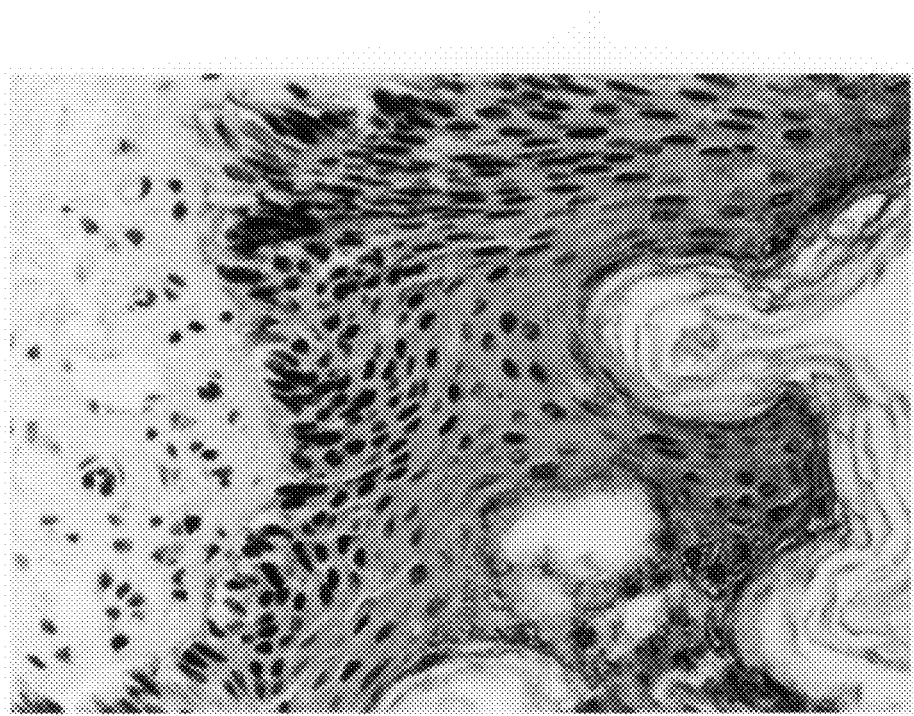

The differences in quality and intensity of immunostaining using the conventional DAB formulations (DAB2) and buffer versus the DAB formulation using the stannous fluoride buffer are depicted in the photomicrographs (FIGS. 4B and 4A, respectively). Table 6 provides the quantification of the data supported by the visual observations that the DAB-$SnF_2$ enhanced formulation produced an enhanced image over the conventional formulations (i.e., DAB1 and DAB2). Table 6 presents the mean intensity differences among the three formulations and their standard deviations.

TABLE 6

Intensity Measurements - Tissue Immunostains with anti-cytokeratin

|  | Enhanced $SnF_2$ DAB | Conventional DAB 1 | Conventional DAB 2 |
|---|---|---|---|
|  | 106.4 | 85.9 | 44.4 |
|  | 191.9 | 78.3 | 32.4 |
|  | 159.2 | 58.6 | 31.8 |
|  | 205.2 | 85.2 | 48.9 |
|  | 90.9 | 50.3 | 30.6 |
|  | 284.7 | 31.3 | 31.4 |
|  | 288.6 | 70.7 | 10.5 |
|  | 344.5 | 30.6 | 18.6 |
| Total: | 1671.4 | 490.9 | 248.6 |
| Mean: | 208.925 | 61.3625 | 31.075 |
| Median: | 198.55 | 64.65 | 31.6 |
| SD: | 90.7808 | 22.4387 | 12.4031 |

Figure 5:
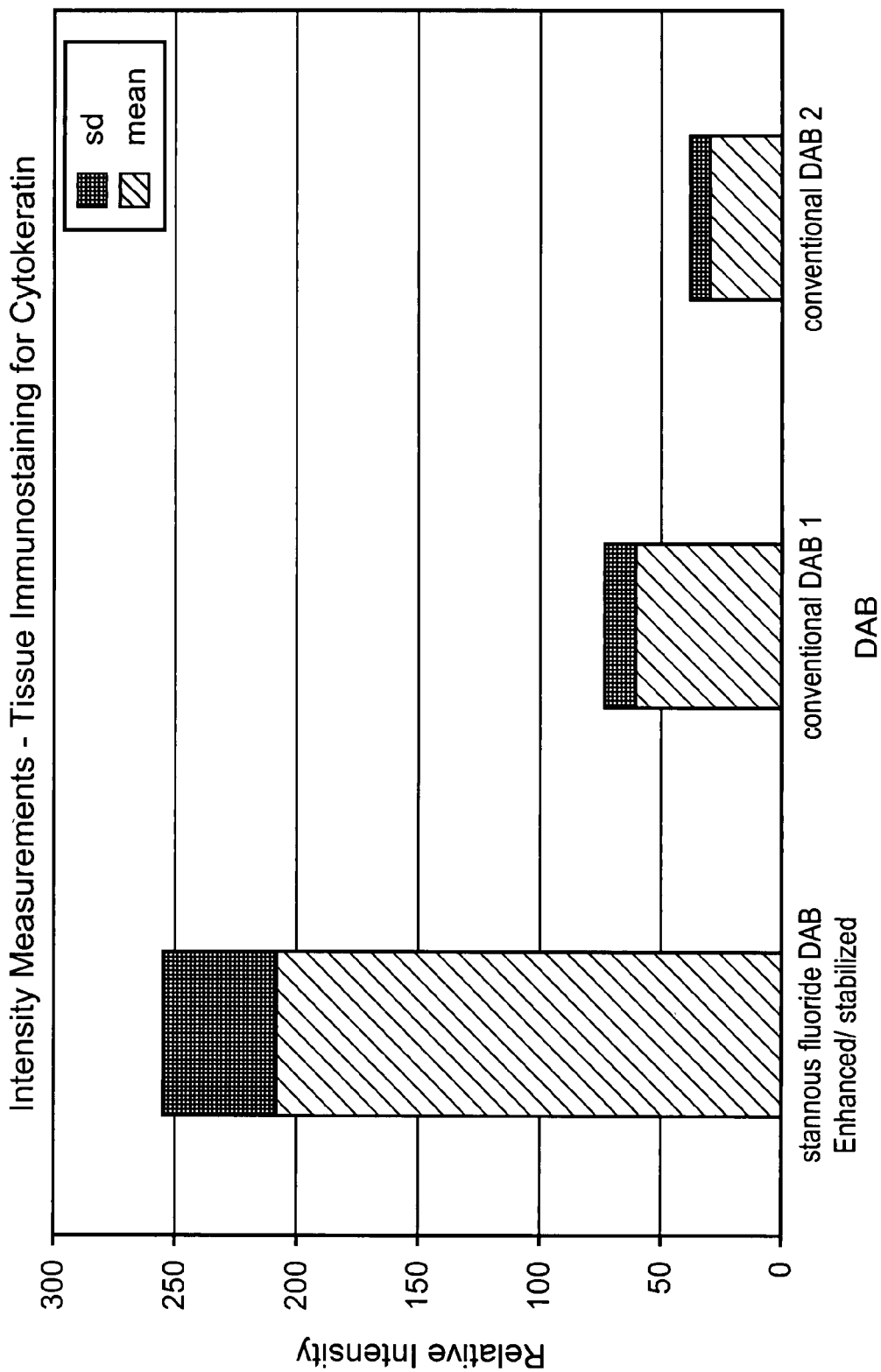
FIG. 5. Histogram comparing the standard deviation (sd) and the mean values of the $SnF_2$ DAB formulation as compared to two conventional DAB formulations (DAB1 and DAB2).

The results in Table 0.6 evidence that the difference between the $SnF_2$ enhanced formulation is statistically significantly higher (highly significant with a $p<0.001$; $p=0.0003$) than the results obtained with DAB using the standard formulations (i.e., DAB1 and DAB2). All three formulations produced statistically different results and the SnF$_2$ formulation yielded the highest mean intensity values, as summarized in FIG. 5.

All referenced cited above are herein incorporated by reference in their entirety.

We claim:

1. A method of conducting an assay for the presence or concentration of an analyte in an aqueous sample comprising: (A) admixing with said sample a heme containing protein which is coupled to a compound which binds specifically to said analyte; (B) removing unbound heme containing protein in said sample after said admixture; (C) admixing a composition comprising a peroxide, a peroxide stabilizing and/or enhancing amount of a stannous halide, a substrate and an alkaline buffer, wherein said composition has a pH of about 8.0 or greater; and (D) measuring the amount of detectable substrate obtained, wherein said detectable substrate obtained is indicative of the presence or concentration of said analyte.

2. The method of claim 1, wherein said heme containing protein is peroxidase, said stannous halide is SnF$_2$ and said peroxide is hydrogen peroxide.

3. The method of claim 1, wherein said compound which specifically binds to said analyte comprises an antibody or antibody fragment, a nucleic acid, a protein, or a hapten.

4. The method of claim 1, wherein said detectable substrate comprises a chemiluminescent compound, a chemifluorescent compound and colorimetric compound.

5. The method of claim 4, wherein said chemiluminescent compound comprises luminol, isoluminol, a polyphenol or a diacyl hydrazide.

6. The method of claim 4, wherein said colorimetric compound comprises 3-amino-9-ethylcarbazole (AEC), 3,3',4,4'-diaminobenzidene (DAB), 3,3',5,5'-tetramethylbenzidine (TMB), 2,2'-azino-di[3-ethylbenthiazoline]sulfonate) (ABTS), 4-chloro-1-naphthol (4CN), 5-aminosalicyclic acid (5AS), o-phenylenediamine (OPD), Hanker-Yates, p-phenylenediamine (PPD), o-dianisidine, or analogs thereof.

7. The method of claim 1, wherein said substrate is a chemiluminescent compound, said heme containing protein is peroxidase, and step (C) further comprises a peroxidase activity enhancer selected from the group consisting of N,N-dimethylindo-(aniline), 2,6-dichlorophenolindo-o-cresol, phenolindophenol, N-methylphenothiazine and mixtures thereof.

8. The method of claim 1, wherein said heme containing protein is a peroxidase, a hemoglobin, a myoglobin, a catalase, a cytochrome oxidase or a territin.

9. The method of claim 1, wherein the composition of step (c) has a pH of about 8.0 to about 10.0.

10. The method of claim 9, wherein the pH is about 9.5.

11. A method for detecting the presence or concentration of a heme containing protein in a sample comprising: (A) adding to said sample a composition comprising (i) a peroxide, (ii) a substrate, (iii) a peroxide stabilizing and/or enhancing amount of a stannous halide, and (iv) an alkaline buffer, wherein said composition has a pH of about 8.0 or greater; and (B) measuring the amount of detectable substrate obtained by said reaction, wherein said detectable substrate is indicative of the presence or concentration of said heme containing protein.

12. The method of claim 11, wherein said detectable substrate is detected by chemiluminescence, chemifluorescence or calorimetric analysis.

13. A method for detecting the presence or concentration of a peroxide in a sample comprising: (A) adding to said sample a composition comprising (i) a heme containing protein, (ii) a substrate, (iii)) a peroxide stabilizing and/or enhancing amount of a stannous halide, and (iv) an alkaline buffer, wherein said composition has a pH of about 8.0 or greater; and (B) measuring the amount of detectable substrate obtained by said reaction, wherein said detectable substrate is indicative of the presence or concentration of said peroxide.

14. The method of claim 13, wherein said detectable substrate is detected by chemiluminescence, chemifluorescence or calorimetric analysis.

15. A method of performing in situ hybridization with a first nucleic acid which is attached to an indicator and wherein said first nucleic acid can hybridize to a second nucleic acid in a cell or a tissue sample obtained from a subject comprising the steps of: (A) obtaining a cell or tissue sample from said subject; (B) digesting said cell or said tissue sample with a proteinase; (C) performing in situ hybridization on said cell or said tissue sample obtained from step (B) with said first nucleic acid which specifically hybridizes to said second nucleic acid; (D) incubating said cell or said tissue sample from step (C) in a composition comprising a peroxide, a heme containing protein, a stannous halide, and an alkaline buffer; and (E) detecting said indicator bound to said first nucleic acid which is reacted by said heme containing protein.

16. The method of claim 15, wherein said indicator comprises a luminescent indicator or a calorimetric indicator.

* * * * *